United States Patent
Godoy et al.

(10) Patent No.: US 10,151,682 B2
(45) Date of Patent: Dec. 11, 2018

(54) AIRBORNE PARTICLE MEASURING DEVICE

(71) Applicant: Teilch LLC, Palo Alto, CA (US)

(72) Inventors: Pedro Godoy, Portola Valley, CA (US); Juan Bardina, Portola Valley, CA (US)

(73) Assignee: Teilch LLC, Palo Alto, CA (US)

( * ) Notice: Subject to any disclaimer, the term of this patent is extended or adjusted under 35 U.S.C. 154(b) by 0 days.

(21) Appl. No.: 15/146,097

(22) Filed: May 4, 2016

(65) Prior Publication Data
US 2017/0328825 A1 Nov. 16, 2017

Related U.S. Application Data

(60) Provisional application No. 62/192,564, filed on Jul. 14, 2015.

(51) Int. Cl.
*G01N 15/14* (2006.01)
*G01N 21/01* (2006.01)
(Continued)

(52) U.S. Cl.
CPC ..... *G01N 15/1434* (2013.01); *G01N 15/0211* (2013.01); *G01N 15/06* (2013.01); *G01N 15/1431* (2013.01); *G01N 15/1456* (2013.01); *G01N 21/01* (2013.01); *G01N 21/53* (2013.01); *G02B 6/12* (2013.01);
(Continued)

(58) Field of Classification Search
CPC ............... G01N 15/1434; G01N 21/01; G01N 2223/05; G01N 2021/0162; G01N 2015/1087; G02B 6/12; G02B 2006/12121
See application file for complete search history.

(56) References Cited

U.S. PATENT DOCUMENTS 3,705,771 A * 12/1972 Friedman ........... G01N 15/1434
250/461.2
3,947,123 A * 3/1976 Carlson .............. G01N 15/1434
356/338

(Continued)

OTHER PUBLICATIONS http://www.junktronix.com/ebay/proddocs/SLM%2520README.pdf.*

(Continued)

*Primary Examiner* — Mohamed K Amara

(57) ABSTRACT

An airborne particle-measuring device quantifies and qualifies contaminants of an air environment in clean-rooms, open spaces, and enclosed spaces such as homes, offices, industrial environments, airplanes in flight, cars and others. The device may include a sensor system, an electronics system, communications and information storage. The sensor system may include a high-power low-wavelength single-frequency continuous laser, an open-cavity high-efficiency mirror having an optical surface tuned to the laser frequency and a flow system that includes a vacuum pump to sample the air. The electronics system may be mounted on a single multilayer PC board with a microprocessor, firmware, electronics and a touch-screen LCD display. Innovations in light source, flow control, analog and digital signal processing, components integration and software allow provision of equipment in a wide range of high-complexity settings that require precise particle measurements.

13 Claims, 16 Drawing Sheets

(51) Int. Cl.
    *G02B 6/12*             (2006.01)
    *G01N 15/02*           (2006.01)
    *G01N 15/06*           (2006.01)
    *G01N 21/53*           (2006.01)
    *G01N 15/10*           (2006.01)
    *G06F 3/0484*         (2013.01)
    *G06F 3/0488*         (2013.01)
    *G01N 15/00*           (2006.01)

(52) U.S. Cl.
    CPC ............... *G01N 2015/0046* (2013.01); *G01N 2015/0693* (2013.01); *G01N 2015/1087* (2013.01); *G01N 2015/1486* (2013.01); *G01N 2021/0162* (2013.01); *G01N 2201/06113* (2013.01); *G01N 2201/12* (2013.01); *G01N 2223/05* (2013.01); *G02B 2006/12121* (2013.01); *G06F 3/0488* (2013.01); *G06F 3/04847* (2013.01)

(56) References Cited

U.S. PATENT DOCUMENTS

| | | | | |
|---|---|---|---|---|
| 4,072,421 A * | 2/1978 | Coyne | G01N 15/1434 | 356/39 |
| 4,523,841 A * | 6/1985 | Brunsting | G01N 15/1436 | 356/340 |
| 4,839,528 A * | 6/1989 | Itoh | G01N 15/1434 | 250/574 |
| 4,842,406 A * | 6/1989 | VonBargen | G01N 15/0205 | 356/336 |
| 5,089,714 A * | 2/1992 | Ludlow | G01N 15/1456 | 250/574 |
| 5,247,461 A * | 9/1993 | Berg | G01N 15/1031 | 324/464 |
| 5,467,189 A * | 11/1995 | Kreikebaum | G01N 15/0205 | 250/574 |
| 5,471,299 A * | 11/1995 | Kaye | G01N 15/1436 | 356/336 |
| 5,675,155 A * | 10/1997 | Pentoney, Jr. | G01N 27/44721 | 204/452 |
| 5,767,967 A * | 6/1998 | Yufa | G01N 15/0205 | 250/458.1 |
| 5,870,186 A * | 2/1999 | Mogan | G01N 15/02 | 250/573 |
| 5,946,091 A * | 8/1999 | Yufa | G01N 15/0205 | 356/336 |
| 6,034,769 A * | 3/2000 | Yufa | G01N 15/02 | 356/335 |
| 6,120,166 A * | 9/2000 | Price | G01J 3/10 | 362/302 |
| 6,177,277 B1 * | 1/2001 | Soini | G01N 15/1434 | 356/72 |
| 6,404,494 B1 * | 6/2002 | Masonis | G01N 21/53 | 250/574 |
| 6,618,143 B2 * | 9/2003 | Roche | G01N 15/1434 | 356/339 |
| 6,836,332 B2 * | 12/2004 | Mosley | G01N 21/3151 | 356/436 |
| 6,967,338 B1 * | 11/2005 | Sickenberger | G01N 15/1459 | 250/461.1 |
| 7,126,687 B2 * | 10/2006 | Hill | G01N 15/0205 | 356/336 |
| 7,324,194 B2 * | 1/2008 | Roche | G01N 1/38 | 356/246 |
| 7,502,110 B2 * | 3/2009 | Saunders | G01N 15/1459 | 356/336 |
| 7,605,389 B1 * | 10/2009 | Doughty | H01J 49/00 | 250/288 |
| 7,914,734 B2 * | 3/2011 | Livingston | B01L 3/5085 | 422/50 |
| 8,085,399 B2 * | 12/2011 | Adams | G01N 15/1459 | 356/338 |
| 8,477,307 B1 * | 7/2013 | Yufa | G01N 21/658 | 356/337 |
| 9,851,291 B2 * | 12/2017 | Silcott | G01N 15/1434 | |
| 9,921,144 B2 * | 3/2018 | Cole | G01N 15/06 | |
| 2005/0243307 A1 * | 11/2005 | Silcott | G01N 15/1459 | 356/73 |
| 2009/0095643 A1 * | 4/2009 | Svetlicic | G01N 15/1031 | 205/792 |
| 2012/0050734 A1 * | 3/2012 | Wennmalm | G01N 21/6408 | 356/301 |
| 2013/0229655 A1 * | 9/2013 | Kaye | G01N 15/0205 | 356/343 |
| 2015/0056909 A1 | 2/2015 | Chien | | |
| 2016/0363520 A1 * | 12/2016 | Braumandl | G01N 15/0205 | |
| 2017/0059485 A1 * | 3/2017 | Yamamoto | G01N 33/582 | |
| 2017/0315046 A1 * | 11/2017 | Du | G01N 15/1434 | |

OTHER PUBLICATIONS http://www.aikencolon.com/kanomax-3910-portable-laser-particle-counter.*
https://www.wateronline.com/doc/particle-counter-0003.*
https://www.trotec24.com/en-bh/measuring-instruments/emission/pc200-particle-counter-incl-cal-certificate.html.*
Non-Final Office Action issued in U.S. Appl. No. 15/582,115, dated Feb. 12, 2018, 19 pages.

* cited by examiner

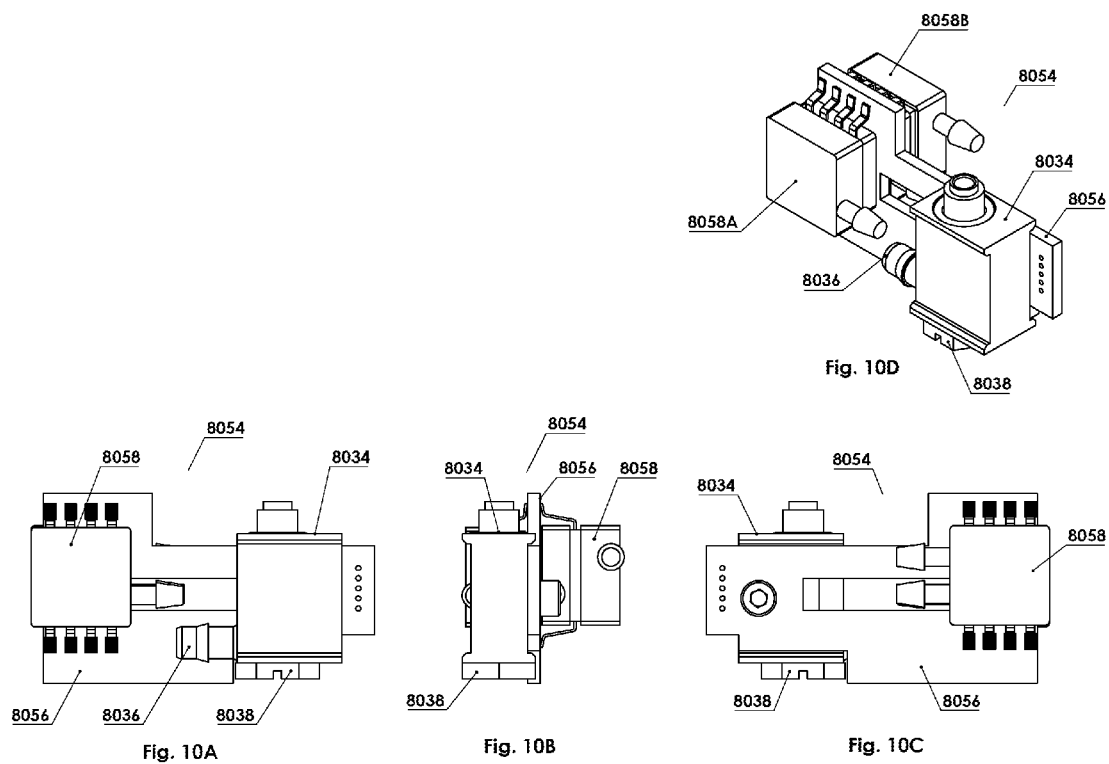

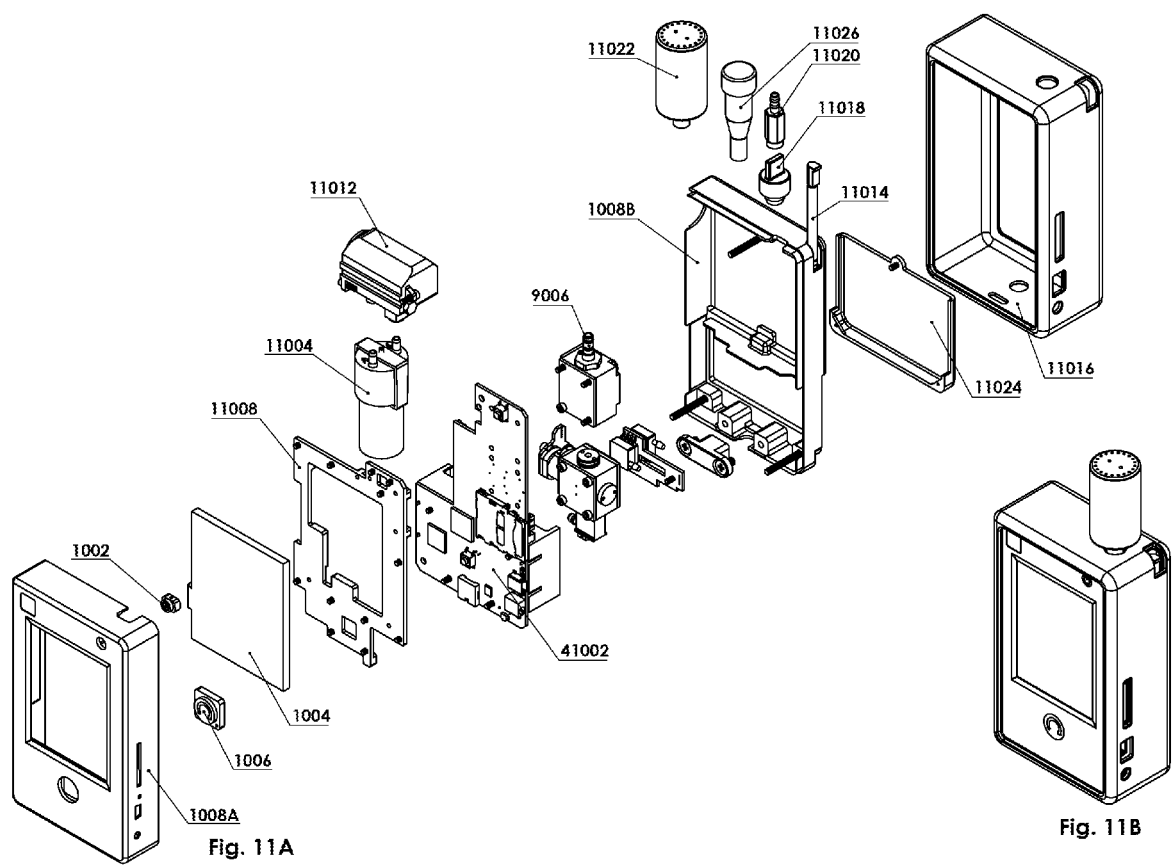

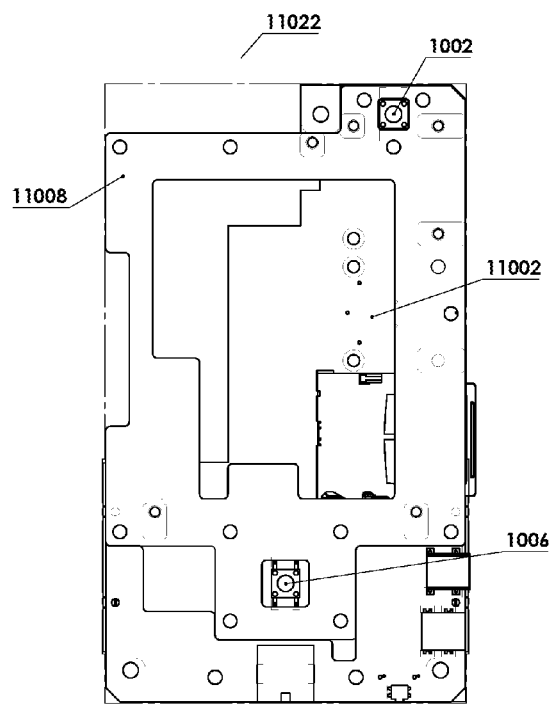
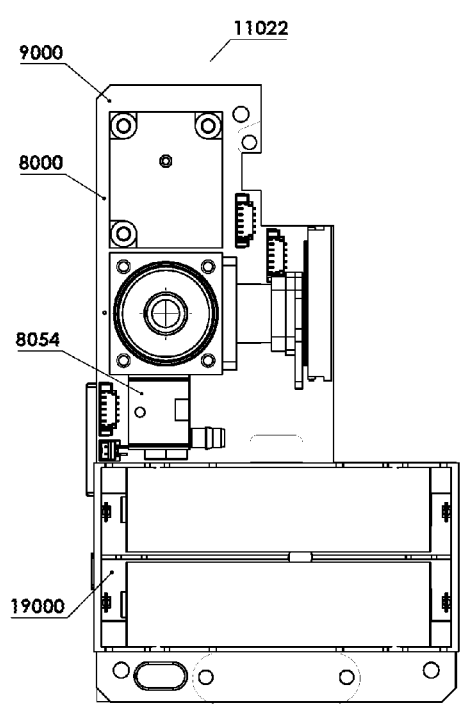
Fig. 19A
Fig. 19B

AIRBORNE PARTICLE MEASURING DEVICE

CROSS REFERENCE TO RELATED APPLICATIONS

This application claims benefit of U.S. provisional patent application Ser. No. 62/192,564, filed Jul. 14, 2015, the entirety of which is incorporated in its entirety by this reference thereto.

TECHNICAL FIELD

The present disclosure generally relates to detection of air contaminants. More particularly, the present disclosure relates to airborne particle measuring devices.

BACKGROUND INFORMATION

Airborne particle measuring devices are instruments used to determine air quality by counting and sizing the number of airborne particles in the air. Such information may then be used to determine the air quality inside a building or in the ambient air. It also is useful in assessing the cleanliness level in controlled environments, such as a cleanrooms.

Any particle measuring device has a limit on the smallest particle size it can detect. This is because, eventually, a particle may be so small that the light scattered by the particle cannot be distinguished from background noise, caused by operation of the device itself. In practical terms, the smallest particle a handheld particle counter can detect is approximately 0.5 microns (500 nanometers).

Portable (but not handheld) particle measuring devices are available that can measure particles small as 0.3 microns. These devices, however, suffer a number of disadvantages that limit their usefulness. Among these disadvantages is their cost. One of these portable particle measuring devices can easily cost $20,000.00 or more. Also, while they are nominally portable, their large size and considerable weight makes them difficult to deploy, transport and store. Additionally, when they are deployed in a cleanroom environment, they may provide surfaces upon which airborne particles may settle and accumulate.

Fixed-installation remote particle measuring systems also have the ability to detect and measure airborne particles of less than 0.5 microns. However, these are large systems, usually deployed on a facility-wide basis to provide continuous monitoring of several locations within the facility. They are only deployed at great cost and after careful evaluation and planning.

Condensation particle counters (CPC) are capable of indirectly detecting nano-particles, in some devices, as small as 2.5 nm. A CPC works by exposing the particles to the super-saturated vapor of a solvent such as butyl alcohol. The cooled, supersaturated vapor condenses upon the particles in droplets, effectively causing a particle to increase in size from, for example, 0.01 microns to 1-2 microns, at which size the particle becomes readily detectable. In addition to being complicated to use, operate and maintain, because a CPC grows all particles to the same size, it is capable only of counting particles and not of measuring and/or reporting their size.

As mentioned above, handheld particle counters produced according to conventional engineering and manufacturing methods have a low signal-to-noise ratio that prevents them from having the resolution necessary to be able to detect airborne particles any smaller than, for example, 0.5 microns. One of the most problematic components of these devices is the sensor. Conventional sensors are incapable of minimizing background noise to the degree necessary to detect particles smaller than 0.5 microns.

Another disadvantage of conventional particle measuring devices is that they do not report the actual size of the particles detected. Instead, the pulse emitted by a detector as it detects a particle is classified within a channel or bucket representing a particular nominal size. For example, in the case of a nominal size of 3.0 microns, there may be significant numbers of particles that are larger or smaller than the nominal size of 3.0 microns. Typically, the variance of all the particles from the nominal size results in a Gaussian size distribution about the nominal size. Conventionally, in selecting which particles are to be classified within the 3.0 micron channel, the processor selects those particles at the peak of the Gaussian curve and to the right and places those in the 3.0 micron channel. All particles to the left of the peak of the curve are placed in the next lower bucket. Thus, even though the device measures the size of each and every particle, once the particles are placed in size channels, the particle size data is lost or at least hidden from the user, and the values reported for the nominal size actually fall within a size range, rather than the actual measured particle sizes. While the use of buckets or channels to classify particles according to size ranges conforms to official standards for particle measuring devices, it is insufficiently precise for many high-complexity situations.

SUMMARY

An airborne particle-measuring device quantifies and qualifies contaminants of an air environment in clean-rooms, open spaces, and enclosed spaces such as homes, offices, industrial environments, airplanes in flight, cars and others. The device may include a sensor system, an electronics system, communications and information storage. The sensor system may include a high-power low-wavelength single-frequency continuous laser, an open-cavity high-efficiency mirror having an optical surface tuned to the laser frequency and a flow system that includes a vacuum pump to sample the air. The electronics system may be mounted on a single multilayer PC board with a microprocessor, firmware, electronics and a touch-screen LCD display. Innovations in light source, flow control, analog and digital signal processing, components integration and software allow provision of equipment in a wide range of high-complexity settings that require precise particle measurements.

BRIEF DESCRIPTION OF THE DRAWINGS

FIGS. 10 A-D provide various views of a pressure sensor assembly in the airborne particle measuring device of FIG. 1.

FIG. 11 provides an exploded internal isometric view of the complete system embodied in the airborne particle measuring device of FIG. 1;

FIGS. 19A-B provide views of an electro-mechanical integration from the airborne particle measuring device of FIG. 1.

DETAILED DESCRIPTION

An airborne particle-measuring device quantifies and qualifies contaminants of an air environment in clean-rooms, open spaces, and enclosed spaces such as homes, offices, industrial environments, airplanes in flight, cars and others. The device may include a sensor system, an electronics system, communications and information storage. The sensor system may include a high-power low-wavelength single-frequency continuous laser, an open-cavity high-efficiency mirror having an optical surface tuned to the laser frequency and a flow system that includes a vacuum pump to sample the air. The electronics system may be mounted on a single multilayer PC board with a microprocessor, firmware, electronics and a touch-screen LCD display 1004. Innovations in light source, flow control, analog and digital signal processing, components integration and software allow provision of equipment in a wide range of high-complexity settings that require precise particle measurements. Sensor and electronics provide for single-stage analog conditioning and digitization, in which a conventional DC gain stage is omitted, for detection of complete spectrum of particle sizes.

Acquisition of a full particle size spectrum enables an entirely new concept for airborne particles in which direct acquisition and data logging of size information for every one and all particles entering the sensor makes possible the complete elimination of size channels, universal among conventional airborne particle counters.

Software classification of particles, rather than the conventional hardware classification, greatly improves reliability and accuracy and provides true particle size profiles. A new combination of software, increased laser power, lower wavelength, high-efficiency mirror, peak detection, high speed analog to digital conversion, measuring of environmental variables, processing power, memory capacity, interactive color touch screen, and overall device size achieves a level of resolution and power not previously attainable with conventional equipment.

Electronic analog peak detection with digital conversion may allow for increased resolution exceeding 16 bits. In embodiments, pulse height analysis pulse (PHA) data may be used to quantify the total number of pulses, the voltage of each pulse and size of the corresponding particle at controlled volume flow rate within the device. It is this real-time generation of information concerning the particulate matter that allows display of quantity versus size in a continuous mode instead of relying on "buckets" of size ranges as prescribed by various standards.

While embodiments of the device have the capability of reporting quantity vs. size in real time, embodiments also include the ability to display particle count and size information in the conventional matter, in size buckets, for particulate matter up to 2.5 microns in size (PM2.5) and for particulate matter up to 10 microns in size (PM10)

Figure 1:
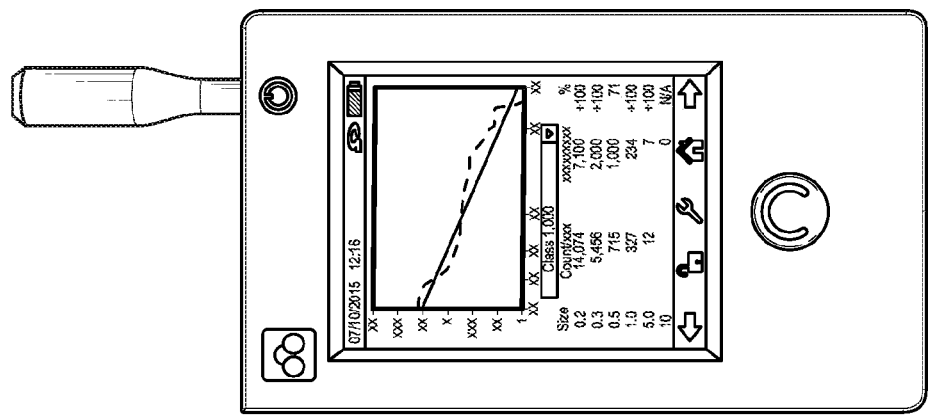
FIG. 1 provides a front view of an airborne particle measuring device.

Turning now to FIG. 1, shown is an airborne particle-measuring device 1000. As shown in FIG. 1, in embodiments, the internal components of the particle-measuring device 1000 may be enclosed within a crushproof, dust proof and highly portable impact-resistant hard case 1008. In embodiments, the case may be fabricated from milled aluminum, although a number of other materials may be suitable for the case.

In embodiments, the device 1000 may include an air inlet (not shown here) equipped with an isokinetic sampling probe 1010. The use of an isokinetic probe at the inlet of the sensor ensures isokinetic flow of the sample air into the sensor. One of ordinary skill will readily recognize that the isokinetic probe 1010 helps to ensure that the air velocity at the sampling point remains the same as the air velocity in the environment being sampled. In embodiments, the device 1000 may be provided with a removable zero-count filter for performing zero-count testing to verify that the device 1000 is in good working order. In embodiments, the air inlet may be a barbed inlet.

In embodiments, the device 1000 may include a data display 1004. In embodiments, the data display 1004 may be an LCD which receives data from the processor and outputs the received data in a format which may vary according to the type of data being displayed and the particular analytic task being performed. FIGS. 3-7 show embodiments wherein the display outputs different portions and aspects of the data measured from a sample. A user interface (GUI) provides a number of possible display layouts as shown in the Figures and described herein below.

In embodiments, the device 1000 may include power button 1002, activation of which powers up the device 1000.

In embodiments, the device 1000 may include a quick/stop button 1006 which initiates air sampling and subsequent analysis of the sample.

Figure 2:
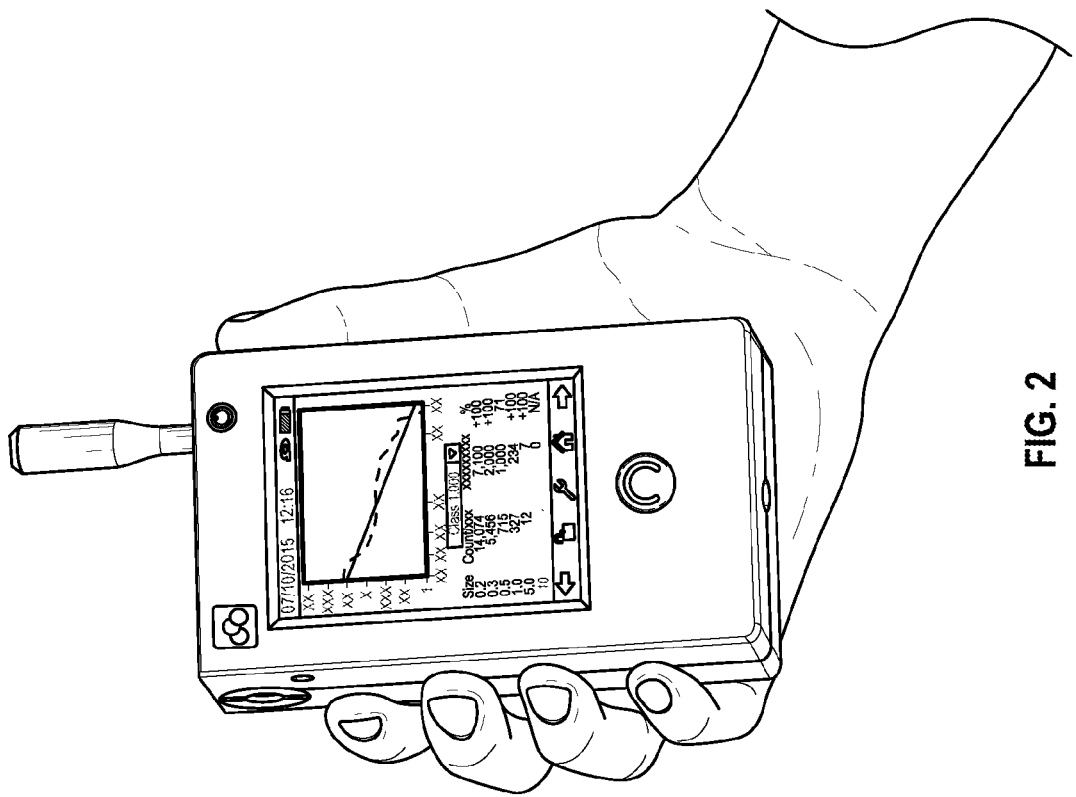
FIG. 2 provides a view of a hand-held embodiment of the airborne particle measuring device of FIG. 1.

FIG. 2 shows the device 1000 being deployed by a user. Additionally, as shown in FIG. 2, the device may include an air outlet 1012.

As described in the background section, conventional airborne particle analysis devices place the measured particles in size channels or "buckets" rather than reporting the actual size of every particle measured. Because of this method of reporting, important air-quality information may be unavailable to the user, with the result that one could be led to believe, from the result reported by a conventional device, that an environment, such as a cleanroom environment was ISO-compliant, when in fact, at least some aspects of the air quality may be out of compliance.

In stark contrast, the present device 1000 is able to acquire and report full size data for every single particle contained in the sample air entering the device 1000, thereby providing a comprehensive in-field particle analysis. In embodiments, environmental counts may be made from the same air sample being measured for particulate contamination. As shown in FIGS. 3-7, the GUI may display an advanced on-screen particle analysis and on-screen full particle data plot.

Figure 3:
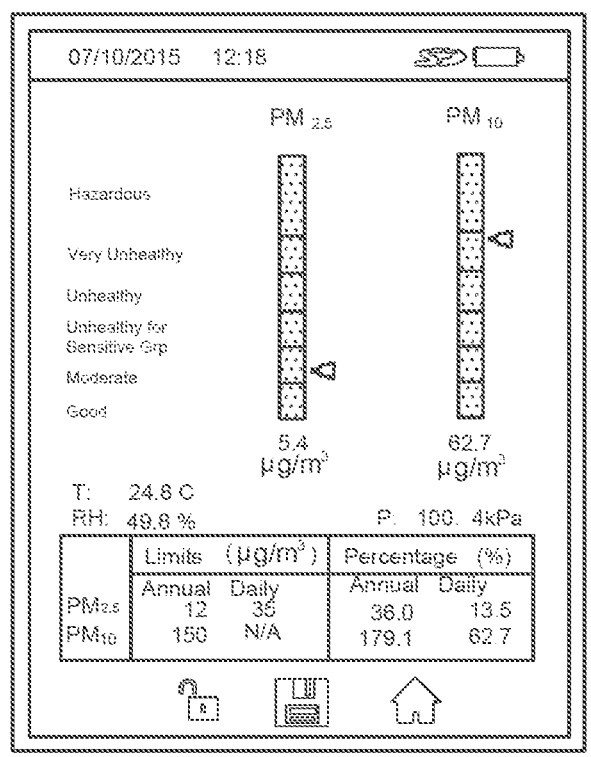
FIGS. 3-7 provide views of several embodiments of graphical user interface from the airborne particle measuring device of FIG. 1.

FIG. 3 shows an embodiment wherein the display outputs data regarding fine particulates less than 2.5 microns in size (PM 2.5) and particulates between 2.5 and less than 10 microns in size (PM 10). A bar chart in the display may show whether measured levels are safe, and if not, how far out of compliance they are. Additionally, as shown, the display may show the sampling date and time, the temperature, relative humidity and barometric pressure at the time of sampling. Additionally, the display may show, for example, a table, giving the actual and percentage limits of PM 2.5 and PM 10 on a daily and an annual basis. Further, the display may show a toolbar by which the user may access additional device functions. The toolbar illustrates another important feature of the display 1004, in that the display 1004 may be a touch screen, interaction with which enables the user to configure the device and to select which data is to be displayed.

In stark contrast to conventional airborne particle measuring devices, embodiments of the present device 1000 may record and report size data for each and every particle that enters the sensor. Additionally, the size data may be exported for post analysis in a computer program such as EXCEL (MICROSOFT CORP., Redmond Wash.), MATLAB (THE MATHWORKS, INC., Natick, Mass.) or in any numerical software package. In embodiments, the data may be exported as a standard text log file. In embodiments, a single log file may contain data for up to 20,000 particles for each sampling period and for unlimited sampling periods. While the device 1000 may acquire and display a continuous particle size spectrum, displaying particle quantity versus size, the user may set fixed channels of particle sizes for display purposes. In embodiments, no limits are placed on the number of size channels.

Figure 4:
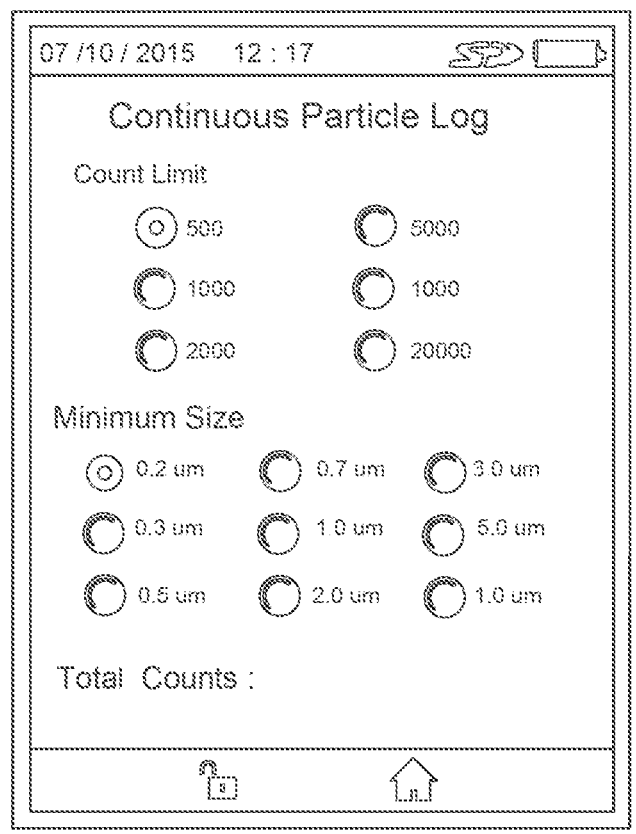

FIG. 4 shows a screen from the display 1004 by which the user can configure parameters for the continuous particle log—one or more of count limit, minimum size and total count.

Figure 5:
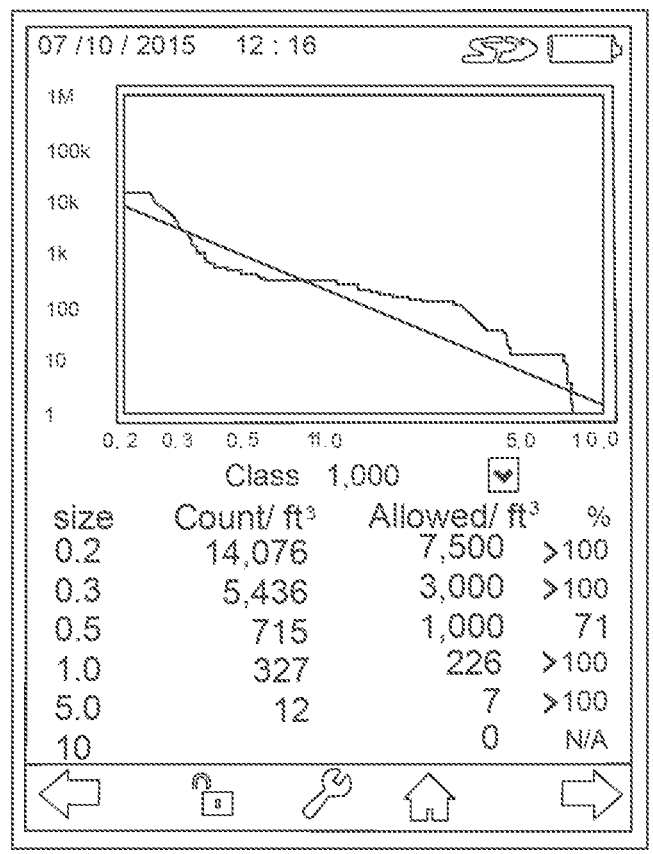

FIG. 5 shows a graph of actual measured particle sizes vs. the ISO standard for the most common particle sizes. In embodiments, adaptive display modes for clean-room and household/office environments are provided. For example, the display 1004 may contain a pulldown menu with which the user may select the particular cleanroom class standard against which the particle counts are to be compared. Here, class 1000 is selected. As shown, the air quality is out of compliance for almost all of the particle sizes displayed.

Figure 6:
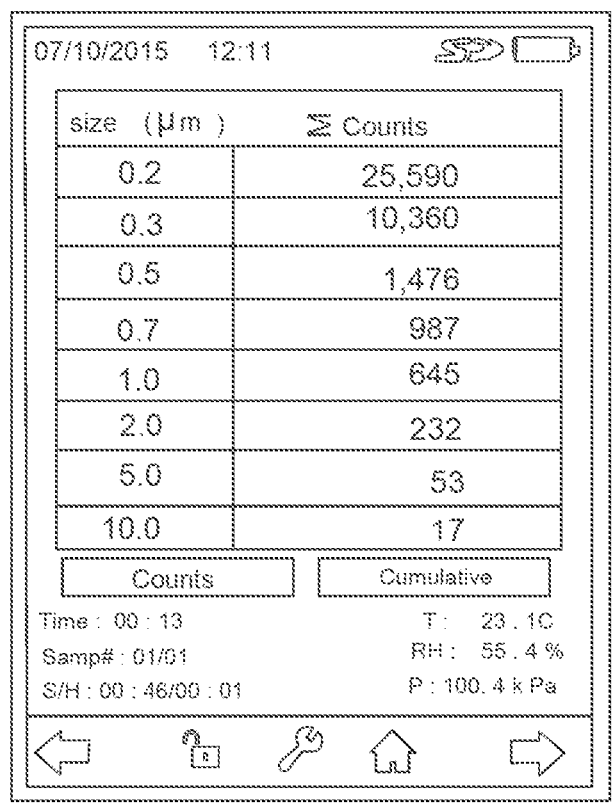

FIG. 6 displays a table showing total counts for common sizes on a single screen.

Figure 7:
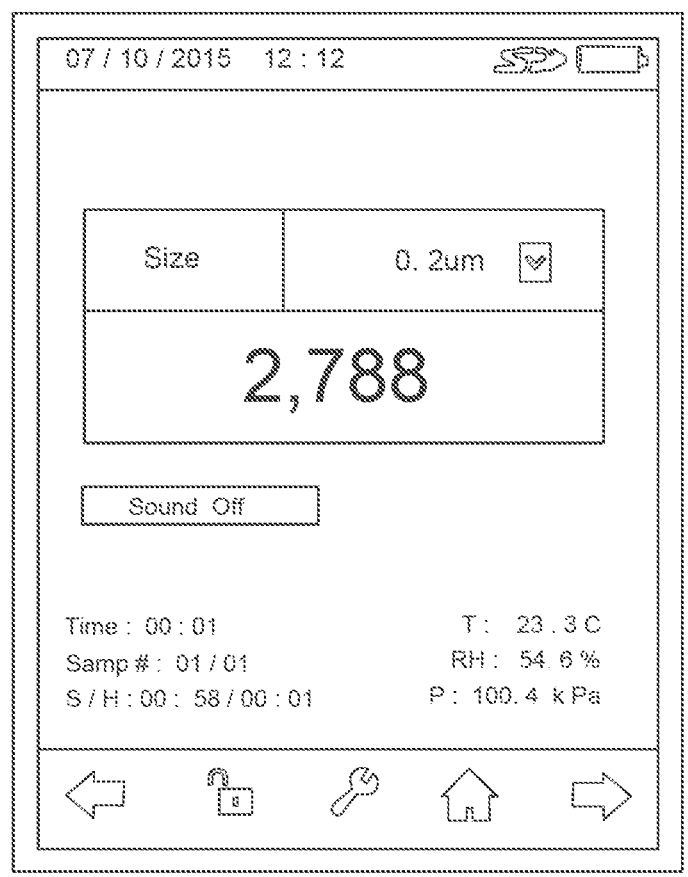

FIG. 7 shows a display of a total count for a single size.

In embodiments, the display may show an on-screen Log-Log plot for particle count versus particle size.

The presently-described instrument 1000 is based on the use of light scattering to detect particles. A high-intensity light source is used to illuminate the particles as they pass through a detection chamber. The particles pass through the light field emitted by the source, scattering the light in the process. The redirected light is then detected by a photodetector. In a particle-measuring device, it is the sensor that performs the central function of detecting airborne particles.

Figure 8:
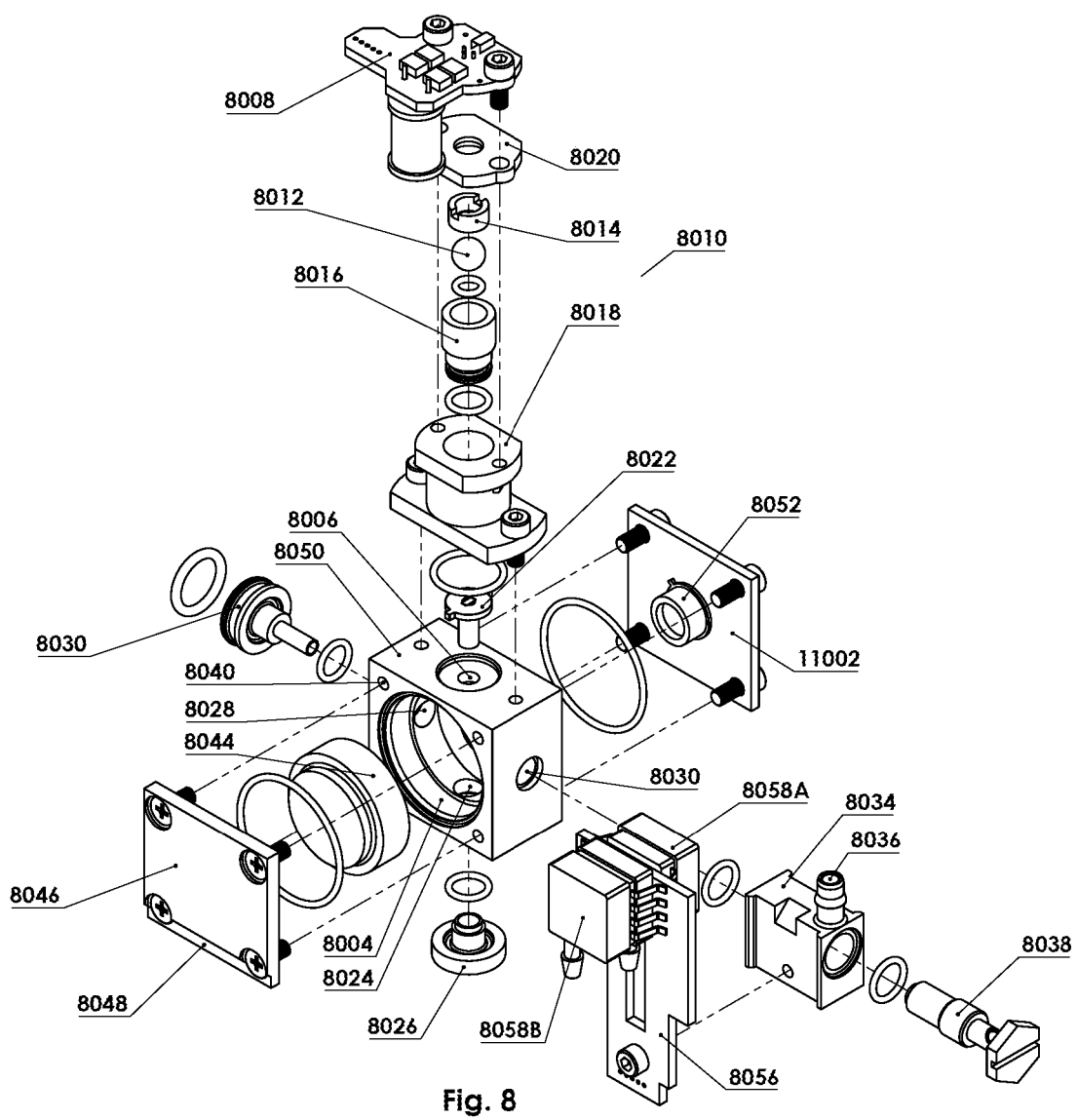
FIG. 8 provides an exploded isometric view of a main particle sensor in the airborne particle measuring device of FIG. 1.

FIG. 8 provides an exploded isometric view of a main sensor sub-assembly 8000 from the particle-measuring device 1000 of FIG. 1. As shown, a sensor body 8002 defines a detection chamber 8004. In embodiments, the sensor body 8002 may be, for example, a cuboid body fabricated from metal stock such as, for example, milled aluminum. In addition to defining the detection chamber 8004, the sides of the sensor body 8002 may define various ports or openings into which the various active components of the sensor sub-assembly 8000 are received.

One side of the sensor body 8002 may define an opening 8006 for receiving a light source. In an embodiment, the light source may be a laser 8008. In an embodiment, the laser 8006 may be a laser diode. In embodiments, the laser 8008 may operate at a wavelength of less than or equal to 500 nm and may have an average power consumption of more than 50 mW. In embodiments, variable laser power allows a significantly increased dynamic range, enabling the device to detect particles in a size range of less than 2 nanometers up to approximately 25 microns.

In embodiments, the laser light source 8006 may be coupled to an optic assembly 8010, the optic assembly being functional to direct light emitted by the laser 8006 into the detection chamber 8004. In an embodiment, the optic assembly 8010 may include an optic such as a ball lens 8012 which is held within at least one ball holder. In an embodiment, the ball lens 8012 may be first contained within an internal ball holder 8014. The assembly of ball lens 8012 and internal ball holder 8014 may then be received by an external ball holder 8016. In an embodiment, the assembly of the external ball holder 8016, internal ball holder 8014 and ball lens 8012 may then be received by a ball lens cover 8018. In an embodiment, the laser may be secured to the optic assembly by means of a laser holder 8020 and a plurality of fasteners. In an embodiment, the fasteners may be a plurality of screws such as socket head cap screws. The socket head cap screws are received, first by holes in the laser PCB 8008, then by openings in the laser holder 8020 and finally by holes in a top surface of the ball lens cover 8018.

In embodiments, a laser window 8022 may transmit the light directed from the laser by the ball lens into the detection chamber. In embodiments, the laser window may be configured to transmit particular wavelengths of light into the detection chamber.

In embodiments, a second opening 8024 in the opposing side of the sensor body 8002 may receive a light trap 8026 for absorbing and stopping the light emitted by the laser 8008.

A third opening 8028 in a third side of the sensor is functional as an inlet for introducing air sampled from the environment under test into the detection chamber. In an embodiment, the inlet opening 8028 may receive a sensor inlet fitting 8030. In an embodiment, the secondary sensor sub-assembly 9000 and the main sensor-sub assembly 8000 may be coupled by means of the sensor inlet fitting 8030. More will be said about the secondary sensor sub-assembly 9000 herein below.

A fourth opening 8032 in a fourth side of the sensor body 8002 may receive a pressure sensor body 8034. In embodiments, the pressure sensor 8034 body may be coupled with the sensor body 8002 by means of the air connector fitting 8030, whereby pressure sensor body 8034 may be fitted to the fourth opening 8032.

A first face 8040 of the sensor body 8002 may contain a fifth opening 8042 which may receive a reflector 8044, such as a mirror. In embodiments, the reflector 8044 may be held by a reflector holder 8046. The reflector holder-reflector assembly 8048 may be coupled with the sensor body 8002 by means of fasteners such flathead screws. In embodiments, the reflector 8044 may be a mirror tuned to the wavelength of the laser. In other words, the reflective surface of the mirror may be configured to be highly reflective in a narrow frequency band that includes the wavelength of the laser. In embodiments, the mirror may be a mirror having a reflective surface upon which one or more dielectric coatings are disposed that tune the reflective surface of the mirror to the laser wavelength. In embodiments, the reflective surface of the mirror may have one or more metallic coatings disposed thereon that tune the reflective surface of the mirror to the laser wavelength.

A second face 8050 of the sensor body 8002 may contain a sixth opening (not shown). A main PCB photodiode 8052 for detecting photons scattered by particles may be received into the sixth opening. In an embodiment, the photodiode may be coupled to the sensor body by means of fasteners such as socket head cap screws. One of ordinary skill will readily appreciate that the light source and the detector and the air stream are oriented at 90-degree angles to each other. As shown, the photodiode 8052 is electro-mechanically coupled to the main PCB 11002.

In embodiments, the laser and other electronics are configured to operate with low background noise and active noise and error suppression and correction, thus allowing sensing of particles of a size range from 25 um down to below 0.2 um with a single device.

Additionally, variable laser power management may increase the range of measured particle sizes and allow the device to operate in different air environments, for example, clean-rooms vs. outdoors.

One of ordinary skill will readily recognize that components shown in FIG. 8 and the remaining figures may be reversibly coupled with appropriate fasteners. In embodiments, the fasteners may constitute threaded fasteners such as screws. In embodiments, the screws may constitute, for example, one or both of socket head cap screws and flat head screws. It will be apparent that the screws are received by appropriate threaded openings in the substrate to which a component is being coupled.

One of ordinary skill will readily recognize that the components of the device 1000 must be coupled with each other in a manner that the sensors remain completely airtight for at least two reasons. First is that the air flow velocity through the device must be constant and must duplicate the air flow found in the environment under test. For this reason, the air flow must not be subject to drafts and currents that may occur as a result of couplings between the components not being tightly sealed. Second, is that the pressure within the device must be maintained at a constant level in order to keep background noise generated by operation of the device to an absolute minimum. For this reason, substantially all of the couplings between components are tightly sealed using seals such as O-rings, which are seated in a groove and compressed during assembly between two or more components, thus creating a seal at the interface of the components.

Figure 9A:
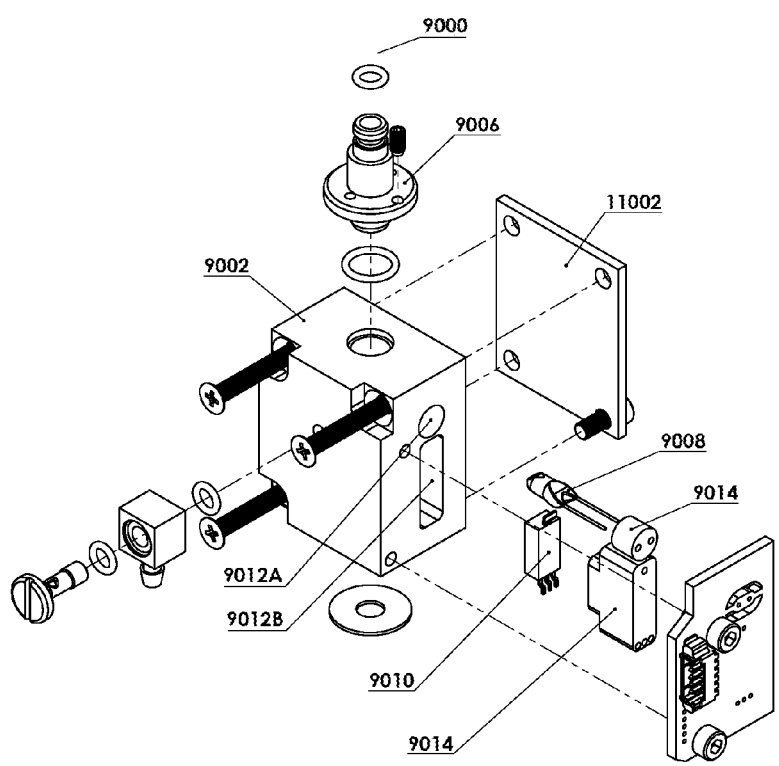
FIGS. 9A and B provide isometric views showing a temperature and relative humidity sensor in the airborne particle measuring device of FIG. 1.
Figure 12A:
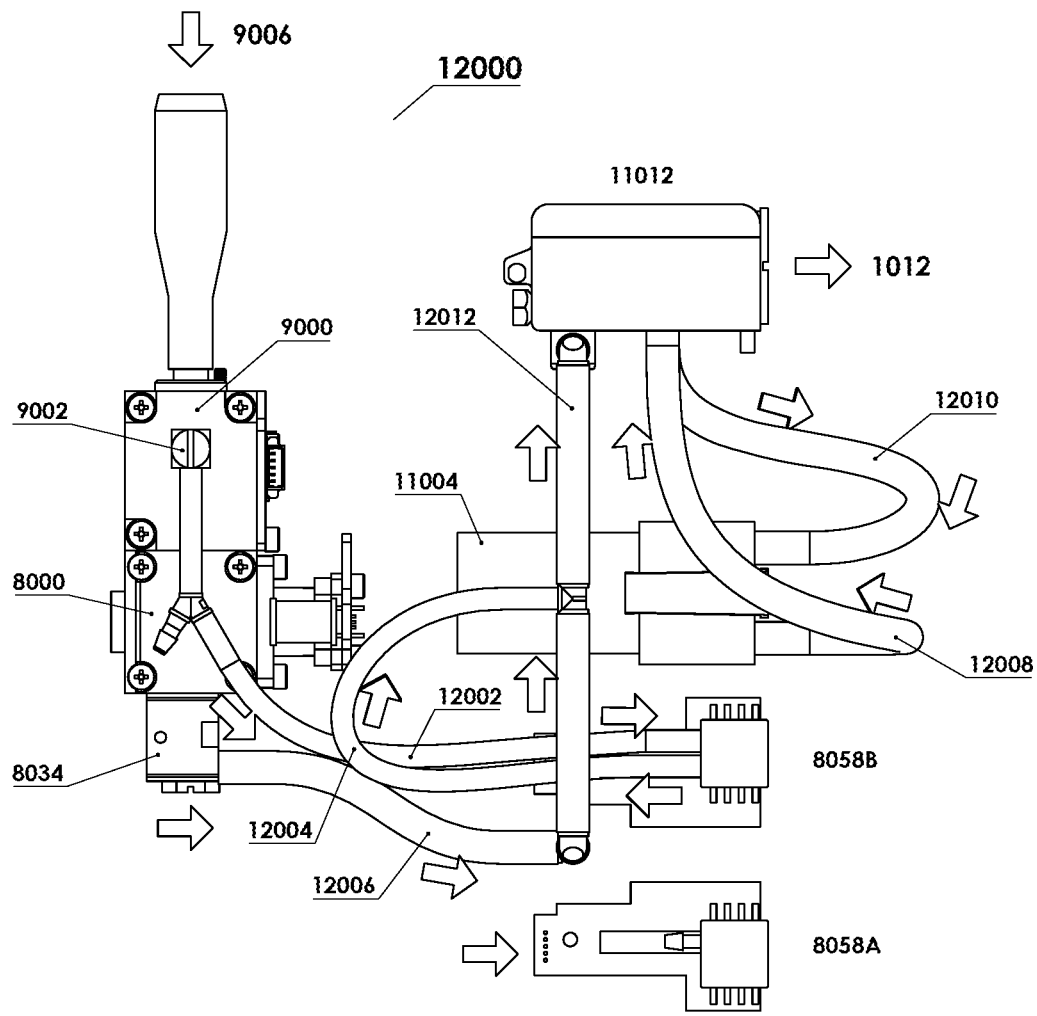
FIGS. 12A-B provide diagrams of air flow through the airborne particle measuring device of FIG. 1.
Figure 12B:
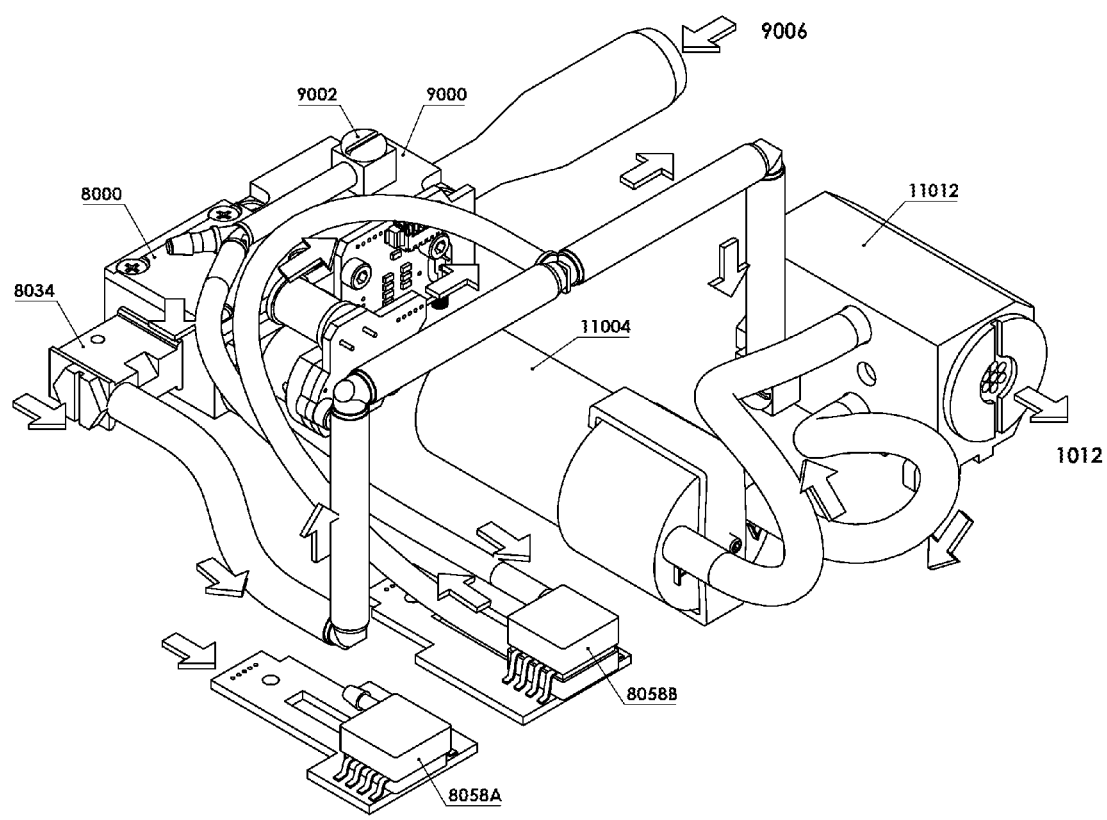
Figure 13:
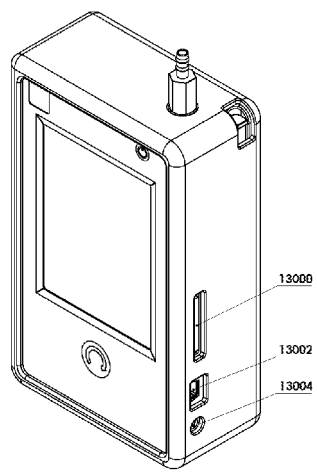
FIGS. 13-15 provide views of the airborne particle measuring device of FIG. 1 contained within a case protector.

Turning now to FIG. 9A, shown is an exploded view of a secondary sensor sub-assembly 9000. In embodiments, the secondary sensor body 9002 may be, for example, a cuboid body fabricated from metal stock such as, for example, milled aluminum. A first side of the secondary sensor body 9002 may define an opening that receives an air inlet screw 9006. As shown in FIGS. 11-13, in embodiments, the air inlet screw 9006 may protrude from the case 1000 to receive a sampling probe 1010 such as an isokinetic sampling probe.

In embodiments, the secondary sensor body 9002 may define one or more openings 9012a and 9012b into which temperature 9008 and humidity 9010 sensors are received. As the sampled air traverses the secondary sensor body 9012, the sensors 9008 and 9010 may make analog determinations of air temperature and humidity. One or more seals 9014 may be used to seal the openings 9012a against air and pressure leaks. The analog temperature and humidity data may be transmitted to a temperature/humidity PCB for digitization.

In embodiments, the secondary sensor 9000 couples to the main sensor 8000 via the air inlet connector fitting 8030. A bottom face (not shown) of the secondary sensor block 9002 defines a port through which sampled air exits the secondary sensor block, whereupon it is received into the detection chamber 8004 via the air inlet connector fitting 8030.

As shown in FIG. 9, a secondary screw barb fitting 9020 may be coupled to the port 9022. Air exiting the secondary sensor sub-assembly 9000 by means of the screw barb fitting may then be directed via a line (not shown here) to a pressure sensor 8034 as described in greater detail herein below.

Internal temperature and relative humidity sensors create a thermal isolation that allows for accurate temperature readings without the need of additional external sensors. The laser photo-diode 8008 is employed to monitor preliminary ambient air conditions by comparing output of the sensor 8000 versus laser light intensity. For example a diminished sensor output for a given amount of laser light would indicate higher air contamination. Data concerning the sensor output may be transmitted to the processor, whereupon the data may be used to compensate for dust and contamination of optical elements, thereby enabling high accuracy and repeatability of measurements made using the device.

Device software is capable of making temperature determinations to better than 0.05° C. accuracy. Temperature compensation of the amplification circuitry allows output to remain constant across the full operating range, thereby enhancing accuracy and repeatability of device measurements.

Device software is capable of making humidity determinations to approximately 3% of full range, allowing for parametric calibration.

Figure 9B:
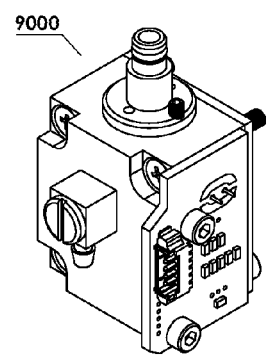

FIG. 9B shows an isometric view of the secondary sensor sub-assembly 9000 completely assembled.

As shown in FIG. 9A the secondary sensor sub-assembly is electro-mechanically coupled to the main PCB 11002.

FIGS. 10A-D provide an isometric view of a pressure sensor assembly 8054, enabling provision of an embedded mass flow sensor, compensated and corrected to display volumetric flow rate, based on pressure drop of the sampled air inside the device. In embodiments, the pressure sensor assembly may include a hollow sensor body 8034. In embodiments, the sensor body 8034 may be, for example, a cuboid body fabricated from metal stock such as, for example, milled aluminum. As shown in FIG. 8, the sensor body 8034 defines an opening from one end of the body to the opposing end of the body 8034. In embodiments, the sensor body 8034 may be coupled to the main sensor body 8002 at the fourth opening 8032 by means of a screw barb fitting 8038. It will be readily appreciated that the join between the two sensor bodies is tightly sealed through the provision of the aforementioned seals. The pressure sensor body 8034 may include at least one barb fitting 8036 that forms a passage from the interior of the sensor to the surrounding environment within the device 1000. During operation of the device, air received from the main sensor body 8002 may be directed to an attached line (shown in FIG. 12) whereby the air may be directed to another part of the device by means of the barb fitting 8036.

Coupled to the pressure sensor body 8034 may be a PCB 8056 having mounted thereon one or more pressure sensors 8058. In embodiments, there may be two pressure sensors. In embodiments, a first pressure sensor 8058a may be mounted on a first side of the PCB. In embodiments, a second pressure sensor 8058b may be mounted on a second side of the PCB. In embodiments, the plurality of pressure sensors 8058 may include a combination of single-port and dual-port sensors. In embodiments, there may be one single-port and one dual-port sensor. The single-port sensor may be used to take an absolute pressure reading and the dual port sensor may be coupled with one or more lines directing air from different regions of the device so that a pressure differential may be measured.

In embodiments, the pressure sensors 8058 may be electro-mechanically coupled with the PCB 8056 by means of a plurality of leads. As shown in FIG. 12, lines may be coupled to the barbed ports of the pressure sensors 8058 in order to direct air to the pressure sensors from various regions of the device, enabling both absolute pressure measurements and differential measurements within the device.

In embodiments, the PCB 8056 may be electro-mechanically coupled with the main PCB 11002. In embodiments, the output of the pressure sensors is an electrical signal proportional to the pressure measured by the sensor 8058. Differential pressure sensors report multiple locations with a single instrument.

In embodiments, device software is capable of absolute pressure determinations to 1 Pascal. 1 Pascal noise-free pressure resolution may allow measurement of pressure differential among isolated areas within a facility without the need of permanent facility-attached equipment.

Data regarding pressure determinations at various locations within the device may be transmitted to the processor whereupon the data are employed by the processor to control flow of sample air through the device. In embodiments, a variable flow rate option may allow for longer battery life in dirty environments and lower sample time in a clean environment.

It will be apparent from the foregoing description that the secondary sensor assembly 9000, the main sensor assembly 8000 and the pressure sensor assembly 8054 are serially coupled, with the sample air:
- first being received from the ambient environment by the secondary sensor assembly;
- next passing to the main sensor assembly for particulate matter analysis; and
- finally passing to the pressure sensor assembly for determination of ambient pressure and a pressure differential.

FIG. 11 provides an exploded internal isometric view of a housing assembly 11000 of the device 1000. In embodiments, contained within a case 1008, the case including a top case 1008a and a lower case 1008b, may be the PCB assembly 11002, the main PCB assembly 11002 including a multilayer PC board, memory and a power supply, as shown in FIGS. 19A and B and 20.

In embodiments, the PC board may have a processor 2000, such as a microcontroller, and enough memory to allow for pattern-learning and contamination qualification. The memory and processor 2000 allow for long-term storage of information and download to external devices. In embodiments, a single low-noise PCB for the sensor and microcontroller may allow for tight electromechanical integration, reducing overall size of device significantly.

In embodiments, the main PCB may include one or more embedded digital potentiometers 20012, 20021, 20026, 20032 allowing for full digital calibration of the device, eliminating the need for adjustment of internal mechanical potentiometers. In embodiments, digital calibration of the device eliminates the necessity of disassembling the device for calibration, with no additional external equipment needed. In embodiments, the device may be self-calibrating when sampling from a mono-dispersed particle source.

In embodiments, the power supply may constitute a battery assembly 19000. In embodiments, the battery assembly 19000 may accept one or more rechargeable lithium-ion batteries. Software-controlled power management allows for extended usage between charges. In embodiments, a single charge may last for over 10 hours, making the device 1000 highly portable.

In embodiments, the memory may constitute a non-volatile memory such as a SD (secure digital card) 11002, upon which the program instructions for driving the device may be stored. Additionally, the memory may provide storage space for the log files containing particle measurement data.

Electro-mechanically coupled to a rear face of the main PCB assembly 11002 may be the secondary sensor sub-assembly 9000 and the main sensor sub-assembly 8000. The pressure sensor assembly 8054 may also be electro-mechanically coupled with the main PCB assembly 11002.

A vacuum pump 11004 may be provided to sample air from the external environment by drawing it into the device 1000 and maintaining a constant air flow velocity and pressure, which duplicates conditions from the external environment, as the sampled air traverses the device 1000. In embodiments, the vacuum pump 11004 may be a rotary vane pump assembly. The vacuum pump 11004 may be electro-mechanically coupled to the main PCB assembly 11002 to receive power and to receive control signals from a processor associated with the main PCB housing assembly upon which a device control program executes. In embodiments, the vacuum pump 11010 may expel air to the external environment via an air outlet filter assembly 11012. In embodiments, variable flow control may be achieved by varying the rate at which the pump 11004 moves sample air through the device.

Electro-mechanically coupled to a front face of the main PCB assembly 11002 may be a LCD touch screen 1004, possibly having a back cover 11008.

Disposed on a face of the LCD touch screen 1004 may be a power button 1002 which may be electro-mechanically coupled to a switch on the front face of the main PCB assembly 11002. A quick/stop button 1006 may be electro-mechanically coupled with a corresponding switch on the front face of the main PCB assembly 11002. Both the power button 1002 and the quick/stop button 1006 may protrude from one or more openings in the top case 1008A.

In embodiments, the device 1000 may be provided with a stylus pen 11014 to facilitate interaction with the device via the LCD touch screen 1004.

In embodiments, the device may include a case protector 11016, into which the case 1008 containing the assembled device components is received.

In embodiments, the air inlet screw 9006 may receive either of:
- an air inlet cap 11018;
- an air inlet barb fitting 11020.

It will be readily appreciated that the air inlet cap 11018 may be deployed when the device 1000 is not in use, and is operative to keep contaminants from entering the device. During use, the device is fitted with the air inlet barb fitting 11020. In embodiments, the air inlet barb fitting may receive one or both of:
- an isokinetic probe with cap 1010; and
- a HEPA filter assembly with cover and cap 11022.

In embodiments, coupled with the bottom case 1008b, there may be a battery back cover 11024, removably attached by means of fasteners such as screws.

For the sake of clarity of illustration, FIGS. 8-11 have omitted lines that couple barb fittings on various device elements to each other and which route sample air from one region of the device to another. Referring now to FIGS. 12A and B, shown are separate view of an air flow diagram 12000 that illustrates a flow path of the air sample being analyzed, with the air flow lines shown. As FIG. 12 shows, the air sample may enter the air inlet 9006 and may proceed to the secondary sensor 9000, as shown in greater detail in FIG. 9. From the secondary sensor, air flow proceeds to the main sensor assembly 8000. From the main sensor 8000, the air flow proceeds to the pressure sensor body 8034. Sample air may exit the pressure sensor body 8034 via a barb fitting 8038. Lines 12006 and 12012 provide a flow path from the pressure sensor body 8034 to the output filter 11012. As the sample air passes through the output filter, it is filtered of particles that have been added to the air as a result of its having passed through the device. Thus, by filtering the air of particles added to the sample air as a result of testing before the air is returned to the external environment, secondary air contamination is avoided.

The sample air emerges from the output filter 11012 and flows to the inlet of the vacuum pump 12008. Finally, air is expelled from an outlet of vacuum pump 12008 and returned, via a line 12008, to the external environment from the device air outlet 1012.

Additionally, as described herein above, sample air is also routed to pressure sensors 8058 for measurement of a pressure differential and for an absolute ambient pressure measurement. Sample air may exit the secondary sensor 9000 via barb fitting 9002, whereupon a line 12002 directs the sample air to both of pressure sensors 8058A and B. Air may exit the pressure sensors for return to the external environment via lines 12004 and 12012.

Figure 14:
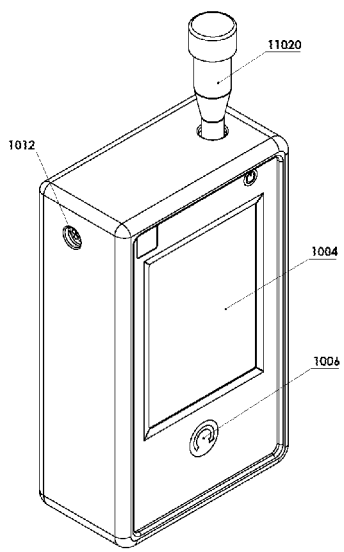
Figure 15:
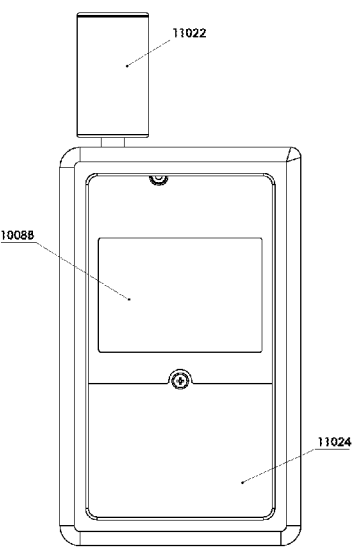

Additionally, sample air may exit the secondary sensor 9000 via a line 12002 coupled with the barb fitting 9002 communicating with the interior of the secondary sensor 9000. The line 12002 provides a path from the secondary sensor 9000 to at least one of the pressure sensors 8058. As shown in FIG. 12, the line 12002 couples the pressure sensor 8058B FIGS. 13-15 provide views of the device 1000 contained within the case protector 11016. FIGS. 13 and 14 provide right front isometric and left front isometric views of the device 1000 in the case protector 11016, respectively. In FIG. 14, the device 1000 is shown fitted with the isokinetic probe 11026 and cap. Additionally, the power button 1002, the LCD touch-screen 1004 and the quick/stop button 1006 are shown.

FIG. 13 shows the device 1000 fitted with the air inlet barb 11020. Additionally, shown are an S/D card slot 13000, a mini-USB port 12002 and a port 12004 for connecting an AC power supply. In embodiments, the device 1000 may be supplied with a USB cable for connecting with a computational device in order to download log data or for battery charging In FIG. 15, the device 1000 is shown fitted with the HEPA filter 11022. Additionally, FIG. 14 provides a full view of the bottom case 1008B and the battery back cover 11024.

Figure 16:
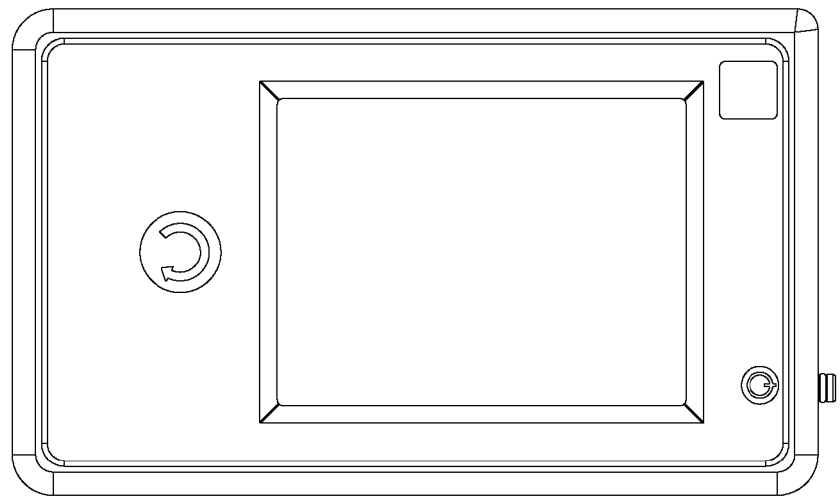
FIGS. 16-18, show further views of the of the airborne particle measuring device of FIG. 1.
Figure 17:
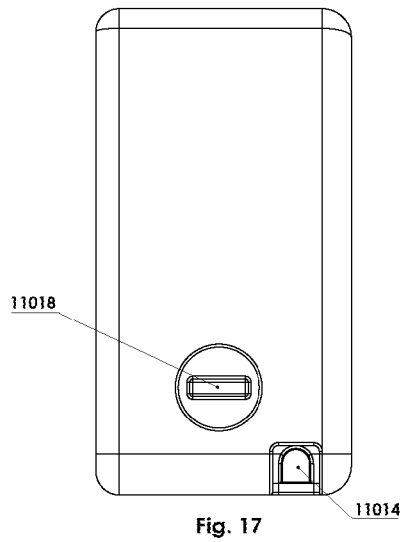
Figure 18:
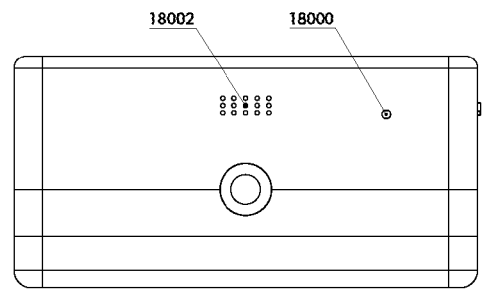

Turning now to FIGS. 16-18, shown are further views of the device 1000. FIG. 16 shows the device 1000 deployed on its side. The air inlet is shown fitted with the air inlet barb 11020. FIG. 17 shows a top view of the device 1000. The device is shown fitted with the air inlet cap 11018 and the stylus probe 11014 resting in the slot provided therefore. FIG. 18 shows a bottom view of the device 1000. Additionally shown are a tripod screw hole 18000 and a series of vent openings 18002 to sink heat generated by device operation into the outer environment, thereby helping to maintain the device operating temperature with a predetermined range.

FIGS. 19A-B provide rear and front views of an electromechanical integration from the airborne particle measuring device of FIG. 1. FIG. 19A provides a rear view of an electromechanical integration of the airborne particle measuring device. Shown is a rear view of main PCB assembly 11022, including:
 an LCD back cover 11008;
 a power button 1002;
 a SDE memory card 11002; and
 a quick/stop button 1006.

FIG. 19B provides a front view of an electromechanical integration of the airborne particle measuring device. Shown is a front view of main PCB assembly 11022, including:
 a secondary sensor sub-assembly 9000;
 a main sensor sub-assembly 8000;
 a pressure sensor sub-assembly 8054; and
 one or more batteries 19000.

Figure 20:
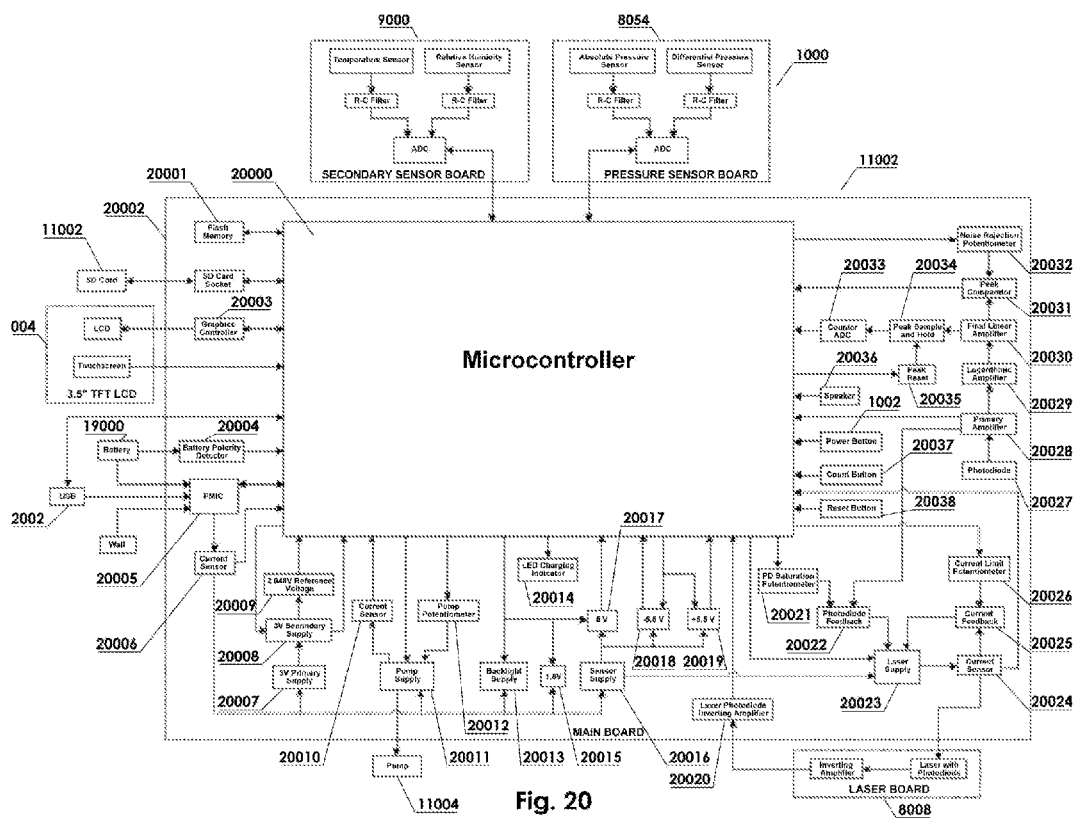
FIG. 20 provides a schematic diagram of the airborne particle measuring device of FIG. 1

Turning now to FIG. 20, a schematic diagram of the airborne particle measuring device 1000 is provided. A main PCB 11002 may include a processor 20000 such as a microcontroller. Electromechanically coupled to the main PCB 11002, there may be any of:
 a secondary sensor board 9000;
 a pressure sensor board 8054;
 a SD card 11002;
 a LCD touchscreen 1004;
 a battery 19000;
 a USB port 12002;
 an AC wall outlet;
 a vacuum pump 11004; and
 a laser PCB 8000.

Embodied on the main PCB 11002, there may be any of:
 a flash memory 20001;
 a SD card socket 20002;
 a graphics controller 20003;
 a battery polarity detector 20004;
 a power management IC (PMIC) 20005;
 one or more current sensors 20006, 20010, 20024;
 a voltage reference 20009;
 3V primary and secondary supplies 20007, 20008;
 a pump supply 20012, backlight supply 20013, sensor supply 20016, laser supply 20033;
 a pump potentiometer 20012, photodiode saturation potentiometer 20021, current limit potentiometer 20026 and a noire rejection potentiometer 20032;
 a laser photodiode inverting amplifier 20020;
 a photodiode feedback 20022 and a current feedback 20025;
 a photodiode 20027;
 a primary amplifier 20028;
 a logarithmic amplifier 20029;
 a final linear amplifier 20023;
 a peak comparator 20031;
 a peak sample and hold 20034;
 a particle counter ADC 20033;
 a peak reset 20035;
 a speaker 20036;
 a power button 1002;
 a count button 20037; and
 a reset button 20038.

In an embodiment, an airborne particle measuring device is provided to an end user in a kit that includes a variety of attachments and peripherals. Embodiments of the kit may include at least one of the following:
 a handheld particle analyzer;
 a power supply;
 an isokinetic probe;
 a barbed probe;
 an inlet filter;

one or more storage media such as a secure digital (SD) memory card. In embodiments they memory card may have a capacity of 2 GB;
a USB cable;
a USB flash drive;
at least one inlet cap;
a case protector; and
a carrying case.

In embodiments, a USB connection via the USB port 12002 can be used for mass storage of data to a USB device. Additionally, the USB connection may be utilized for a firmware upgrade and for a slow charge of the battery (500 mA). In embodiments, the kit may also include at least one battery.

In embodiments, the AC connection may be connected to an AC power source such as a power supply. Additionally, the AC connection can be used to a fast battery charge (2.5A).

Actual use of the airborne particle measuring device may include one or more of the following:
  Power up the device by pressing the power button and holding for a predetermined time interval. In embodiments, the predetermined time interval may be 3 seconds;
  Select an operating mode. In embodiments, available operating modes may include:
    Clean room particle analysis for cleanroom certification and monitoring;
    Continuous Particle log wherein complete particle log data is saved to media such as a SD card;
    Air quality analysis of particulate matter; and
    Differential pressure sampling.
  After the operating mode is selected, the user need only follow the on-screen instructions.
  To purge the sensor, the user first may install an inlet filter, after which he/she runs any count cycle with the pump ON for a predetermined time period. In embodiments, the predetermined time period may be one minute.

Based on the foregoing description, the person of ordinary skill will appreciate that the airborne particle measuring device has the previously unknown capabilities of:
  being able to measure a specific particle size (within +−2 nanometers);
  being able to obtain quantity vs. size in a continuous scale instead of 6 buckets of particles larger than a specific size (called "channels" in the industry);
  being able to display PHA (pulse height analyzer) data: quantity of pulses versus pulse voltage; and
  being able to measure down to 0.2 um (200 nanometers).

Flowing from the above unique device capabilities are a number of important advantages, previously unattainable in the art:
  actual particle identification and identification of a potential source for each particle and/or particle type detected;
  more precise determination of class level (ISO standard);
  the ability to calibrate on-site calibration as well as calibration of other counters; and
  closer to industry requirements.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

The invention claimed is:

1. An airborne particle sensing device comprising:
at least one particle sensor, said at least one particle sensor comprising:
  a single high-power laser light source that emits light at a single wavelength in a range of less than or equal to 500nm;
  a reflector having a reflective surface tuned to a frequency band that includes the single wavelength of said laser; and
  a photodetector that detects photons emitted by said laser and reflected toward said photodetector by said reflector, the photons being scattered as the light emitted by said laser strikes particles suspended in an air sample, said photodetector generating a pulse for each scattered photon detected;
wherein the device further comprises:
a memory having stored therein instructions executable by the processor for:
  counting each generated pulse and calculating a size for the particle corresponding to each pulse; and
  implementing on said display a graphical user interface that reports a particle size for each particle counted on a continuous scale in real time;
wherein at least said at least one particle sensor, said processor, said memory and said display are integrated as a handheld particle analyzer.

2. The device of claim 1, further comprising:
an ambient condition sensor; and
a pressure sensor;
wherein said particle sensor, said ambient condition sensor and said pressure sensor are coupled in series.

3. The device of claim 2, wherein said ambient condition sensor comprises:
at least one temperature sensor; and
at least one relative humidity sensor.

4. The device of claim 2, wherein said pressure sensor comprises:
at least one pressure sensor for measuring a pressure differential; and
at least one pressure sensor for measuring ambient pressure.

5. The device of claim 1, said pressure sensor comprising a flow sensor for measuring pressure drop of sampled air as it traverses said flow path within said device, wherein data from said flow sensor is utilized by said processor to compensate and correct volumetric flow rate.

6. The device of claim 1, further comprising a vacuum pump for drawing an ambient air sample into an air inlet of said device and for pumping the ambient air sample along a flow path defined by said device.

7. The device of claim 1, further comprising computer-readable instructions embodied in said memory, which when executed by said processor perform at least one of: acquiring a full particle size spectrum; directly acquiring and logging size information for every one and all particles entering the sensor; incorporating pulse height analysis (PHA) of quantity of pulses versus pulse voltage and particle size within the device at a controlled volume flow rate; displaying quantity of particles versus particle size on a continuous scale in real time; measuring a specific particle size within +/−2 nanometers; and measuring particles having a minimum size of 0.2 μm (200 nanometers).

8. The device of claim 1, further comprising a cuboid sensor body, said cuboid sensor body defining a sensing chamber, said cuboid sensor body further defining a single opening on each face of said cuboid sensor body, each such opening communicating with the sensing chamber, wherein each of said laser light source, said reflector and said photodetector is fixedly received by a separate one of said openings such that each one of said laser light source, said reflector and said photodetector is disposed at 90 degrees to the remaining ones;

wherein a flow path of the air sample traverses opposing ones of said openings such that the flow path is disposed at 90degrees to each of said laser light source, said reflector and said photodetector; and wherein a light sink is fixedly received at an opening opposing that opening wherein the laser light source is received.

9. The device of claim 1, wherein said laser light source comprises a laser diode having an average power consumption of at least 50 milliwatts (mW).

10. The device of claim 1, wherein said reflector comprises:

a mirror having a reflective surface upon which one or more dielectric coatings are disposed that tune the reflective surface of the mirror to the laser wavelength.

11. The device of claim 1, wherein said device detects particles in a size range of approximately 25 microns to 200 nanometers.

12. The device of claim 1, wherein said display further comprises a graphical user interface, whereby a user employs a touch interface to select between a plurality of operating modes.

13. The device of claim 1, wherein power to said laser light source is variable, resulting in an increased dynamic range, thereby expanding the range of particle size detectable with said device.

\* \* \* \* \*